United States Patent
Doladé Guardia

[19]

[11] Patent Number: 5,813,974
[45] Date of Patent: Sep. 29, 1998

[54] DEVICE FOR WOMEN SUFFERING FROM INCONTINENCE

[76] Inventor: José Manuel Doladé Guardia, Castellnou, 37, 1°, 1ª, Barcelona, Spain

[21] Appl. No.: 769,154

[22] Filed: Dec. 18, 1996

[30] Foreign Application Priority Data

Dec. 19, 1995 [ES] Spain ...................................... 9503200

[51] Int. Cl.⁶ ...................................................... A61F 2/00
[52] U.S. Cl. ........................ 600/29; 600/30; 128/DIG. 25
[58] Field of Search .................... 600/29, 30, 31, 600/32; 128/DIG. 25, 885, 887

[56] References Cited

U.S. PATENT DOCUMENTS

| 4,634,421 | 1/1987 | Hegemann | 604/34 |
| 5,352,182 | 10/1994 | Kalb et al. | 600/30 |
| 5,476,434 | 12/1995 | Kalb et al. | 600/30 |
| 5,513,659 | 5/1996 | Buuck et al. | 128/885 |

FOREIGN PATENT DOCUMENTS

| 92/06731 | 4/1992 | WIPO . |
| 92/19192 | 11/1992 | WIPO . |
| 93/24075 | 12/1993 | WIPO . |

*Primary Examiner*—John P. Lacyk
*Assistant Examiner*—Rosiland Kearney
*Attorney, Agent, or Firm*—Darby & Darby

[57] ABSTRACT

The device comprises a cylindrical sleeve provided, at one end, with an extension for closing the neck of the bladder, which extension has transverse openings for communicating with the axial hole of the sleeve, and having, at the opposite end, a removable plugging means, for the said axial hole, and in that it also has a semi-rigid rod provided with a rounded end and with a flange and a holding grip at the other end, for the introduction of the cylindrical sleeve until the neck of the bladder has been closed.

11 Claims, 5 Drawing Sheets

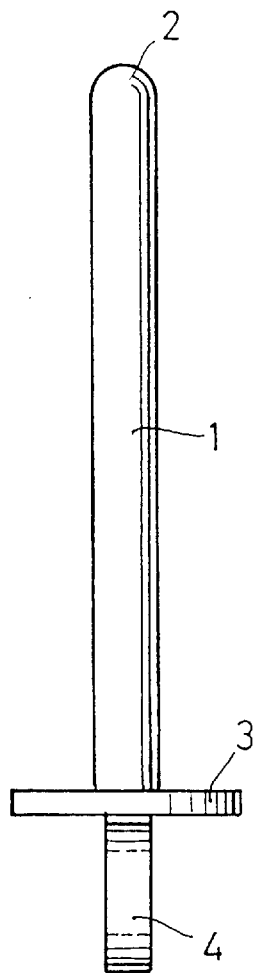
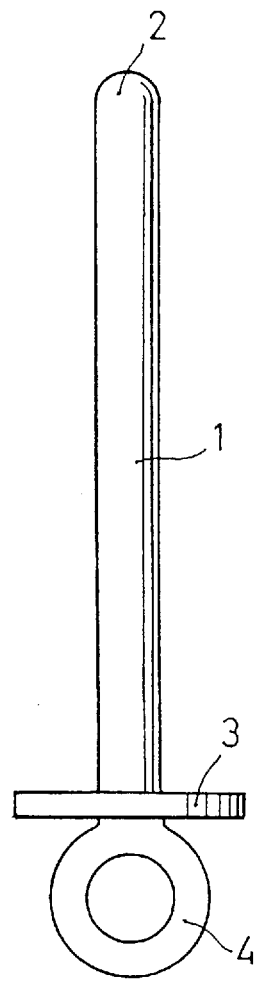
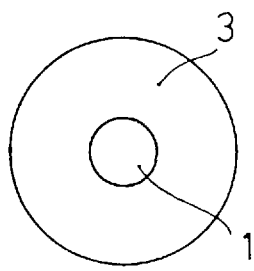
FIG.1  FIG.2
FIG.3

DEVICE FOR WOMEN SUFFERING FROM INCONTINENCE

The present invention relates to a device for women suffering from incontinence, which brings substantial features of novelty and inventive step to the subject for which it is intended.

The aim of the device forming the subject-matter of the present invention is, in cases of feminine incontinence, to provide the patient with a simple and practical means of avoiding the effects of said incontinence, enabling the flow of urine to be controlled by the user as desired.

The device forming the subject-matter of the present invention is basically formed by a cylindrical sleeve, the top of which is provided with a closure head for the neck of the bladder, which head has openings communicating with the inside of the sleeve which is inserted from the outside into the patient's body until it reaches a stop position, and which has a small closure plug, preferably connected to the sleeve by a laminar extension, which enables the device to be kept closed, as desired by the patient, until, by opening the lower plug, it is possible to control the emission of urine without having to withdraw the device once it has been positioned.

In order to introduce the device, a small rod is provided which can be introduced into the sleeve and which is sufficiently rigid and strong to be able, with the aid of a small lower grip, to be used manually for the introduction of the device for controlling incontinence.

The device is preferably produced from a silicone rubber material or the like which, apart from its known features of a low coefficient of friction, can additionally be sterilised and cleaned and also recycled.

In order to clarify the invention, some explanatory drawings of the present invention are appended by way of example.

FIGS. 1, 2 and 3 are side, front and plan views, respectively, of the device forming the subject-matter of the present invention.

FIGS. 1 to 3 show the applicator element of the incontinence device, comprising a preferably cylindrical rod 1 produced from a material having a certain rigidity, the end 2 of which is rounded and which is provided with a stop flange 3 near its lower end and with a small grip 4 which may be in the form of a holding and/or recovery ring.

Figure 11:
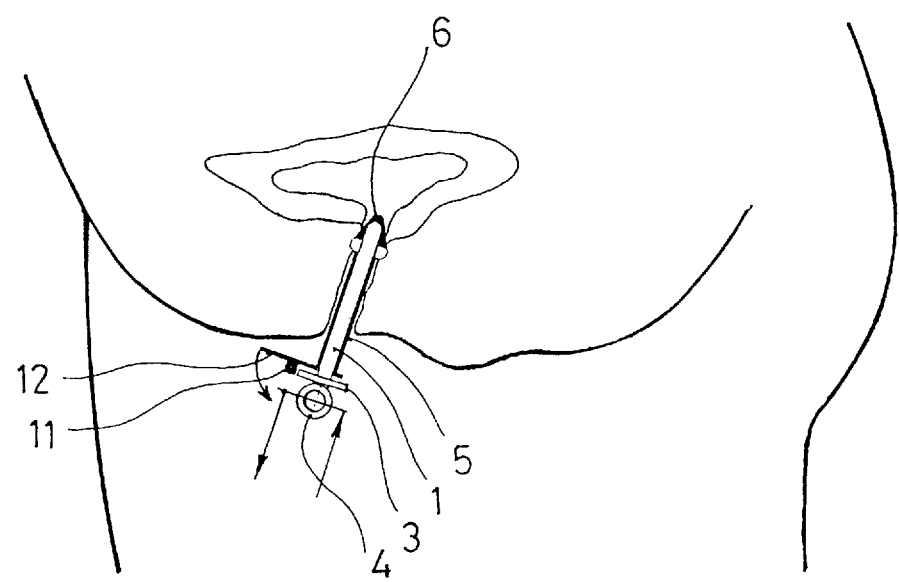
FIG. 11 shows diagrammatically the application of the feminine incontinence device forming the subject-matter of the present invention.

The closure element of the incontinence device comprises a cylindrical sleeve 5 provided, at its upper end, with a closure head 6 which is substantially frustoconical and which is rounded both at the base and at the apex and is provided with various transverse communication openings, such as 7, 8 and 9, preferably at two levels, which communicate with the axial hole 10 of the sleeve 5. The mentioned closure element can be introduced into the position for plugging the neck of the bladder, and so positioning the closure head 6 within the junction of the bladder and the urethra as shown in FIG. 11. The top of the closure head 6 extends into the bladder, while the remainder of the closure head 6 and the cylindrical sleeve 5 lies within the urethra. As shown in FIG. 11, the plugging of the axial hole 10 effected by means of a lower plugging means which may be formed by a projection 11 of an appendage 12 which is an extension of the lower portion of the actual casing 5, thus enabling plugging to be achieved without requiring elements which are separate and therefore easily mislaid.

Figure 9:
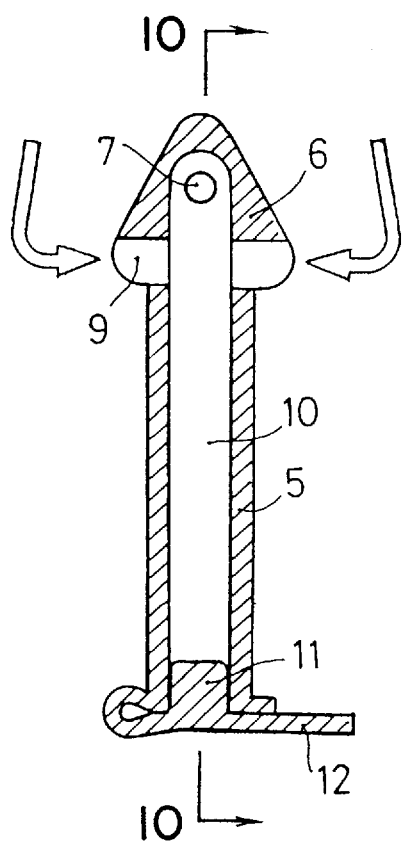
FIGS. 9 and 10 are each sections through the feminine incontinence device in the closed position.
Figure 10:
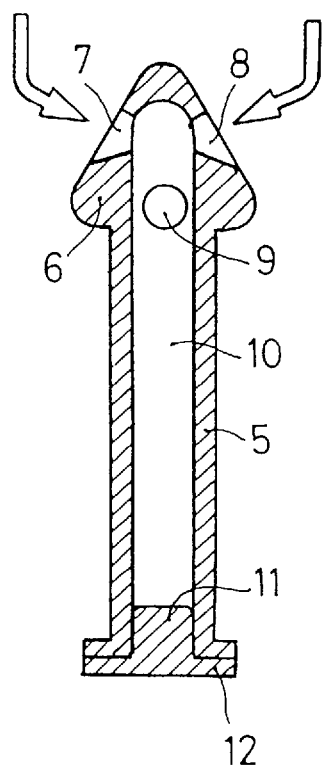

As shown in FIGS. 9 and 10, the appendage 12 is a flexible extension of the cylindrical sleeve 5, capable of bending such that the projection 11 plugs and seals the lower end of the cylindrical sleeve 5. The projection 11 has a substantially identical cross-section as the axial hole 10, as shown in FIGS. 9 and 10, which substantially seals the axial hole 10 when the projection 11 is positioned therein. Bending of the appendage 12 to insert and remove, respectively, the projection 11 selectively seals and unseals the axial hole 10 to prevent or provide, respectively, passage through the axial hole or passage 10 for the flow of urine.

Figure 4:
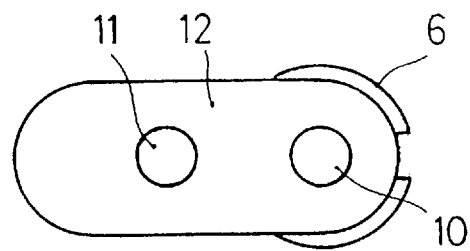
FIGS. 4, 5, 6 and 7 are, respectively, a bottom view, two longitudinal sections and a top view of an embodiment of the device for feminine incontinence forming the subject-matter of the present invention.
Figure 5:
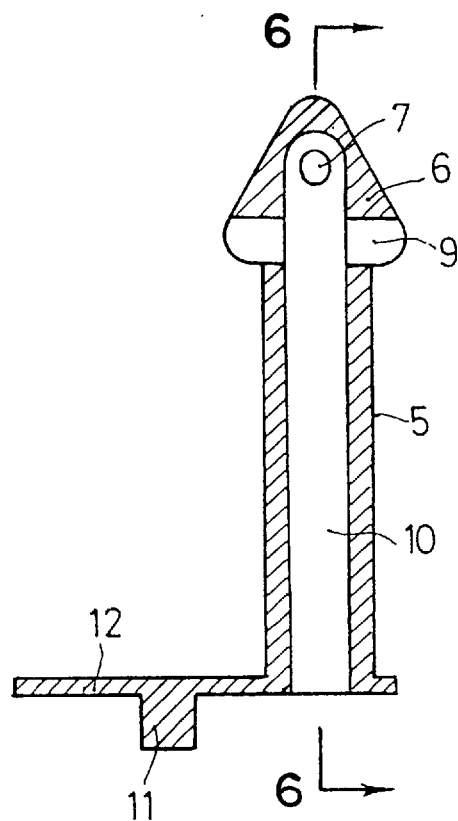
Figure 6:
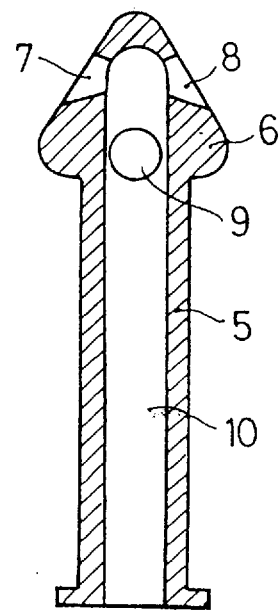
Figure 7:
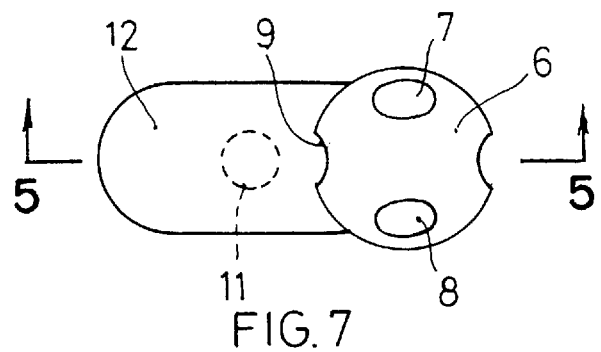
Figure 8:
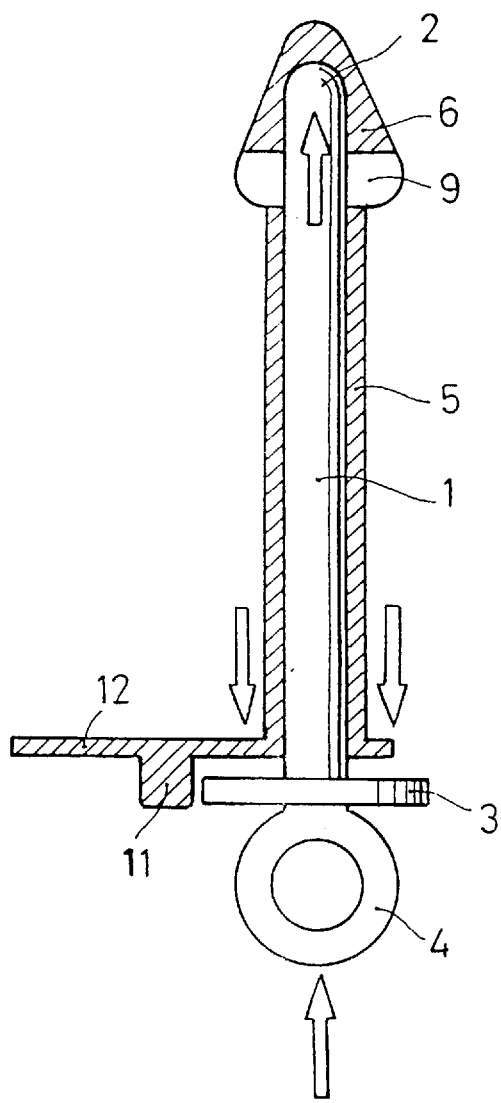
FIG. 8 is a longitudinal section through the incontinence device with its internal applicator rod.

The positioning of the incontinence device is effected, as shown in FIG. 8, by manipulating the internal rod 1 accommodated in the hole 10 of the sleeve 5. The mentioned introduction takes place until a stop position on the user's body is reached, at which moment the axial hole of the sleeve 5 is closed so that the device can correctly carry out its function of controlling incontinence.

As and when desired by the user, the flow of urine can be permitted by unplugging the axial duct 10 without having to remove the incontinence device in its entirety.

The device forming the subject-matter of the present invention may be produced from a suitable material, such as silicone rubber, which has a small wall thickness and can be sterilised and cleaned as well as recycled.

I claim:

1. Device for women suffering from incontinence, comprising a cylindrical sleeve having an axial hole extending therethrough and provided, at one end, with a frustroconical-shaped end extension for abutting the neck of the bladder, wherein the end extension has transverse openings for communicating with the axial hole of the cylindrical sleeve, and having, at the opposite end, a removable plugging means for plugging the said axial hole, wherein the plugging means plugs the opposite end, at a lower end of the cylindrical sleeve, and the plugging means is formed by a projection of a resilient laminar extension of said lower end of the cylindrical sleeve, wherein the lower end is remote from the end extension which abuts the neck of the bladder; and wherein the cylindrical sleeve also has a semi-rigid rod provided with a rounded end and with a flange and a holding grip at the other end, for the introduction of the cylindrical sleeve until the neck of the bladder has been abutted by the end extension.

2. Device for women suffering from incontinence, according to claim 1, wherein the end extension of the cylindrical sleeve has a substantially rounded frustoconical structure with various axially spaced openings communicating with the axial hole of the cylindrical sleeve.

3. Device for women suffering from incontinence, according to claim 1, wherein the cylindrical sleeve is composed of silicone rubber and has thin walls.

4. Device for women suffering from incontinence, comprising a cylindrical sleeve having an axial hole extending therethrough and provided, at one end, with an end extension for abutting the neck of the bladder, wherein the end extension has transverse openings for communicating with the axial hole of the cylindrical sleeve, and having, at the opposite end, plugging means integrally attached to the opposite end for removably sealing the axial hole at the opposite end, and wherein the plugging means plugs the opposite end, at a lower end of the cylindrical sleeve, and the plugging means is formed by a projection of a resilient laminar extension of said lower end of the cylindrical sleeve, wherein the lower end is remote from the end extension which abuts the neck of the bladder; and wherein the cylindrical sleeve also has a semi-rigid rod provided with a rounded end and with a flange and a holding grip at the other end, for the introduction of the cylindrical sleeve until the neck of the bladder has been abutted by the end extension.

5. A device for women suffering from incontinence, comprising:

a cylindrical sleeve having an axial hole extending therethrough and having a first end and a second end, each with a respective axial opening to the axial hole;

a frustroconical-shaped head having at least one opening therein, positioned on the first end, for being positioned within the junction of the bladder and the urethra; and a flexible extension member, integrally connected to the second end, having a projection, wherein bending of the flexible extension member allows the projection to plug and seal the axial opening at the second end.

6. The device of claim 5, wherein the at least one opening of the frustoconical-shaped head and the axial openings in the first and second ends form a passage for the flow of urine upon selective unsealing of the axial opening at the second end by selective removal of the projection therefrom.

7. The device of claim 5, wherein the at least one opening in the frustoconical head is transverse to and is connected to the axial opening of the first end of the cylindrical sleeve for communicating with the axial hole of the cylindrical sleeve.

8. The device of claim 5, wherein the frustoconical head is substantially rounded.

9. The device of claim 5, wherein a portion of the projection has a substantially identical cross-section as the axial opening in the second end to substantially seal the axial opening in the second end when the portion of the projection is positioned therein.

10. The device of claim 5 wherein the cylindrical sleeve is composed of silicone.

11. A kit for a woman suffering from incontinence, comprising:

a closure element to be positioned in the urethra of the woman, the closure element including:

a cylindrical sleeve having an axial hole extending therethrough and having a first end and a second end, each with a respective axial opening to the axial hole;

a frustroconical-shaped head having at least one opening therein, positioned on the first end, for abutting the neck of the bladder at the junction of the bladder and the urethra; and a flexible extension member, integrally connected to the second end, having a projection, wherein bending of the flexible extension member allows the projection to plug and seal the axial opening at the second end; and an elongated rod having a rounded end for closing the at least one opening of the frustoconical-shaped head when the elongated rod is positioned within the cylindrical sleeve during introduction of the closure element into the urethra and the neck of the bladder, to prevent the flow of urine during the introduction.

\* \* \* \* \*